United States Patent
Reinke et al.

(10) Patent No.: US 10,453,566 B2
(45) Date of Patent: Oct. 22, 2019

(54) METHOD FOR RECONCILING MEDICAL DATA CAPTURED ON ONE DEVICE WITH A STRUCTURED TEST ADMINISTERED ON ANOTHER DEVICE

(71) Applicant: Roche Diagnostics Operations, Inc., Indianapolis, IN (US)

(72) Inventors: Robert E. Reinke, Indianapolis, IN (US); Jose Salazar-Galindo, Noblesville, IN (US)

(73) Assignee: Roche Diabetes Care, INc., Indianapolis, IN (US)

( * ) Notice: Subject to any disclaimer, the term of this patent is extended or adjusted under 35 U.S.C. 154(b) by 474 days.

(21) Appl. No.: 14/204,224

(22) Filed: Mar. 11, 2014

(65) Prior Publication Data

US 2014/0324465 A1    Oct. 30, 2014

Related U.S. Application Data

(60) Provisional application No. 61/816,282, filed on Apr. 26, 2013.

(51) Int. Cl.
*G16H 10/65*      (2018.01)
*G16H 10/60*      (2018.01)
*G16H 50/70*      (2018.01)

(52) U.S. Cl.
CPC .............. *G16H 10/65* (2018.01); *G16H 10/60* (2018.01); *G16H 50/70* (2018.01)

(58) Field of Classification Search
CPC .... G06F 19/3418; G06F 19/36; G06F 19/345; G06F 19/3406; A61B 5/14

(Continued)

(56) References Cited

U.S. PATENT DOCUMENTS 8,099,074 B2    1/2012    Ebner et al.
8,229,353 B2    7/2012    Shiga et al.
(Continued)

FOREIGN PATENT DOCUMENTS

EP        2491855         8/2012
JP    2006304833 A  *  11/2006
(Continued)

OTHER PUBLICATIONS

Demidowich et al. "An Evaluation of Diabetes Self-Management Applications for Android Smartphones." Journal of Telemedicine and Telecare; 18: 235-238 (2012).*

(Continued)

*Primary Examiner* — Virpi H Kanervo
(74) *Attorney, Agent, or Firm* — Harness Dickey

(57) ABSTRACT

A method for analyzing diabetes related information by a diabetes management application residing on a computing device. The method may include: receiving a data entry over a communication link from a blood glucose meter, where the data entry includes a glucose measurement and an indicator of a pre-established activity associated with the glucose measurement; evaluating the data entry in relation to a subject structured test based in part by comparing the indicator from the data entry with collection events associated with the subject structured test; identifying the data entry as compatible with the subject structured test when the data entry correlates with a given collection event specified by the subject structured test; identifying the data entry as non-compatible with the subject structured test when the data entry does not correlate with the given collection event specified by the subject structured test; and inputting the data entry into a logbook.

20 Claims, 8 Drawing Sheets

(58) Field of Classification Search
USPC .................................. 600/365, 309; 705/2, 3
See application file for complete search history.

(56) References Cited

U.S. PATENT DOCUMENTS

| | | | |
|---|---|---|---|
| 8,257,653 B2* | 9/2012 | Drucker | A61B 5/743 |
| | | | 422/401 |
| 8,472,913 B2 | 6/2013 | Ebner et al. | |
| 2003/0009088 A1 | 1/2003 | Korth et al. | |
| 2004/0054263 A1* | 3/2004 | Moerman | A61B 5/0002 |
| | | | 600/300 |
| 2007/0060796 A1 | 3/2007 | Kim | |
| 2007/0100222 A1 | 5/2007 | Mastrototaro et al. | |
| 2008/0119705 A1* | 5/2008 | Patel | G06F 19/3412 |
| | | | 600/347 |
| 2009/0106297 A1* | 4/2009 | Wright | H04H 60/37 |
| 2010/0016700 A1 | 1/2010 | Sieh et al. | |
| 2010/0218132 A1 | 8/2010 | Sori et al. | |
| 2010/0228111 A1 | 9/2010 | Friman et al. | |
| 2011/0125530 A1* | 5/2011 | Drucker | A61B 5/743 |
| | | | 705/3 |
| 2011/0178820 A1* | 7/2011 | Soni | A61B 5/0002 |
| | | | 705/3 |
| 2012/0095309 A1* | 4/2012 | Price | G06F 19/3462 |
| | | | 600/365 |
| 2012/0095317 A1* | 4/2012 | Strickland | A61B 5/0022 |
| | | | 600/365 |
| 2012/0266251 A1 | 10/2012 | Birtwhistle et al. | |
| 2012/0276843 A1 | 11/2012 | Yuasa | |
| 2013/0172688 A1 | 7/2013 | Allen et al. | |
| 2013/0172709 A1 | 7/2013 | Mears et al. | |
| 2013/0197320 A1 | 8/2013 | Albert et al. | |
| 2013/0285832 A1 | 10/2013 | Takahashi | |
| 2013/0316645 A1 | 11/2013 | Li et al. | |
| 2013/0344813 A1 | 12/2013 | Ebner et al. | |
| 2014/0088393 A1* | 3/2014 | Bernstein | G06F 19/322 |
| | | | 600/365 |

FOREIGN PATENT DOCUMENTS

| | | |
|---|---|---|
| WO | WO2008/048582 | 4/2008 |
| WO | WO2012048829 | 4/2012 |
| WO | WO2013/069894 | 5/2013 |
| WO | WO2013/069910 | 5/2013 |

OTHER PUBLICATIONS

Deltec Cozmo Insulin Pump (Model 1800)—User Manual: XP055148876; (2008). URL: http://WWW.smiths-medical.com/Upload/products/product_related_docs/diabetes/40/5506-51CCoszmoManual_model_1800.pdf.

\* cited by examiner

| | Event Flag Reconciliation | |
|---|---|---|
| Meter Event Flags | Compatible Structured Test Flags | Incompatible Structured Test Flags |
| Before Meal/ Pre-prandial | Before Breakfast, Before Lunch, Before Teatime, Before Dinner, Low bG, High bG, After Low bG, After High bG | After Breakfast, After Lunch, After Teatime, After Dinner, Bedtime |
| After Meal/ Post-prandial | After Breakfast, After Lunch, After Teatime, After Dinner, Low bG, High bG, After Low bG, After High bG | Before Breakfast, Before Lunch, Before Teatime, Before Dinner, Bedtime |
| Fasting | Fasting, Bedtime, Before Breakfast, Low bG, High bG, After Low bG, After High bG | After Breakfast, Before Lunch, After Lunch, Before Teatime, After Teatime, Before Dinner, After Dinner, Bedtime |
| Bedtime | Bedtime, Low bG, After Low bG, High bG, After High bG | Before Breakfast, After Breakfast, Before Lunch, After Lunch, Before Teatime, After Teatime, Before Dinner, After Dinner |
| Other / Casual | Low bG, After Low bG, High bG, After High bG, Mid-sleep | Before Breakfast, After Breakfast, Before Lunch, After Lunch, Before Teatime, After Teatime, Before Dinner, After Dinner, Bedtime |

FIG. 6

METHOD FOR RECONCILING MEDICAL DATA CAPTURED ON ONE DEVICE WITH A STRUCTURED TEST ADMINISTERED ON ANOTHER DEVICE

CROSS-REFERENCE TO RELATED APPLICATIONS

This application claims the benefit of U.S. Provisional Application No. 61/816,282, filed on Apr. 26, 2013. The entire disclosure of the above application is incorporated herein by reference.

FIELD

The present disclosure relates to a method for reconciling data captured on a medical device with a structured test administered on another device. More particularly, reconciling a glucose measure taken by a blood glucose meter with collection events for a structured test being performed on another device.

BACKGROUND

For people with diabetes, successful management of one's condition requires monitoring the effects lifestyle changes can have in both the short term and the long term. Regular testing of blood glucose level (bG) is an important way to monitor such effects. For example, an individual suffering from diabetes may periodically measure their glucose level using a specialized electronic meter, called a blood glucose meter.

More recently, diabetes management applications have been developed to help the individual track lifestyle changes and, even, glucose measures. Such applications may be used to collect information regarding the individual's meals, glucose measures, drug dosage, exercise, and other suitable information. In addition, the application may allow the individual to perform various structured tests that analyze the data being stored.

A diabetes management application is typically disposed on a device separate from the blood glucose meter. For example, the application may be disposed on a computing device, such as a mobile phone, a personal digital assistant, a tablet, or other similar devices. People often rely on their portable communication device as the primary means for planning, scheduling and communicating with others. As a result, most portable communication devices are equipped with sophisticated software which provides user-friendly means for viewing and inputting data. Accordingly, a person with diabetes may wish to wirelessly transmit the results of a blood glucose measurement from their glucose meter to their portable communication device in order to display, analyze or report on the data. This section provides background information related to the present disclosure which is not necessarily prior art.

SUMMARY

This section provides a general summary of the disclosure, and is not a comprehensive disclosure of its full scope or all of its features.

A method for analyzing diabetes related information by a diabetes management application residing on a computing device. The diabetes management application is implemented as computer executable instructions executed by a computer processor of the computing device.

The method may include: retrieving, by the diabetes management application, requirements for a subject structured test from among a plurality of structured tests being stored in a test repository on the computing device, each of the plurality of structured tests specifies one or more collection events at which a glucose measurement is required for the structured test, wherein the diabetes management application is implemented as computer executable instructions executed by a computer processor of the computing device; receiving, by the diabetes management application, a data entry over a communication link from the blood glucose meter, wherein the data entry includes a glucose measurement and an indicator of a pre-established activity associated with the glucose measurement; evaluating, by the diabetes management application, the data entry in relation to the subject structured test based in part by comparing the indicator from the data entry with the collection events associated with the subject structured test; identifying, by the diabetes management application, the data entry as compatible with the subject structured test when the data entry correlates with a given collection event specified by the subject structured test; identifying, by the diabetes management application, the data entry as non-compatible with the subject structured test when the data entry does not correlate with the given collection event specified by the subject structured test; and inputting, by the diabetes management application, the data entry into a logbook residing in a data store on the computing device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 6 illustrates an example event flag reconciliation table;

Corresponding reference numerals indicate corresponding parts throughout the several views of the drawings.

DETAILED DESCRIPTION

Figure 1:
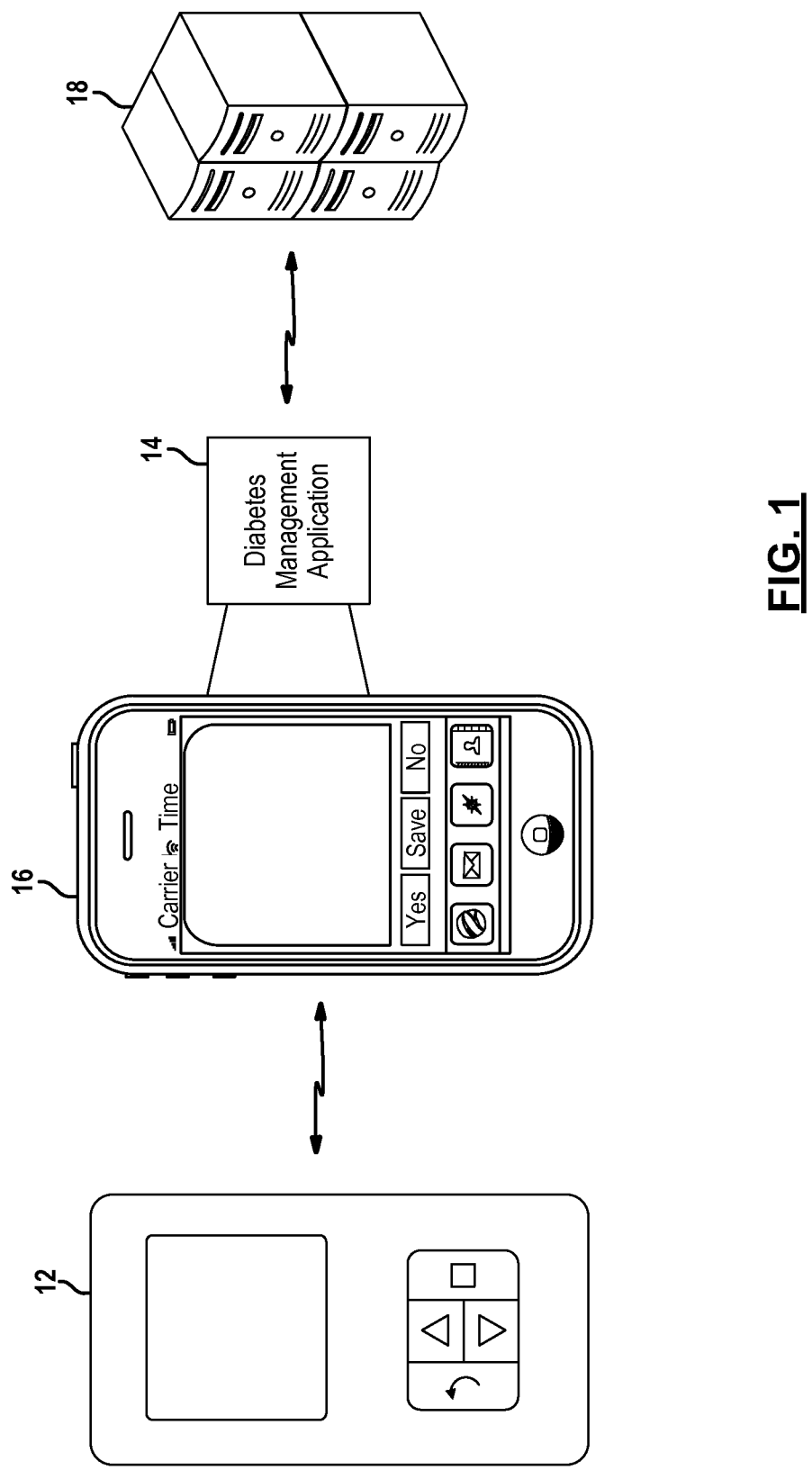
FIG. 1 is a diagram depicting a handheld glucose meter in data communication with a diabetes management application residing on a portable computing device, such as a mobile phone.

The present disclosure will now be described more fully with reference to the accompanying drawings. With reference to FIG. 1, a handheld glucose meter 12 is in data communication via a communication link with a diabetes management application 14. The glucose meter 12 is configured to receive a sample of blood from a user and determine a blood glucose measure. One or more blood glucose measures may in turn be transmitted to the diabetes management application 14 for further processing via the communication link.

The diabetes management application 14 may reside on a portable computing device, such as a mobile phone 16 or a computer. Alternatively, the diabetes management application 14 may be native to a remote server 18 with its user interface presented on the mobile phone 16.

Data may be transferred to and from the glucose meter 12 using a wireless or wired communication link. For example, the wireless communication link may include the Bluetooth wireless technology standard (e.g., low energy feature of Bluetooth 4.0), a WiFi network connection or other suitable wireless connections. With regard to the wired connection, the glucose meter 12 may be physically connected to the portable computing device via a cable. The glucose meter 12 transfers data over the physical connection, and the data can be stored in a memory within the portable computing device. The portable computing device may be configured to transmit data received from the glucose meter 12 to another computing device. For example, if the glucose meter 12 transfers the data to a computer, the computer may transfer the data to the mobile phone 16.

The diabetes management application 14 may communicate one or more glucose measures to the remote server 18. For example, upon receiving the glucose measures from the glucose meter 12, the diabetes management application 14 determines whether to communicate the glucose measure to the remote server 18. The diabetes management application 14 may automatically communicate the glucose measure to the remote server 18. Alternatively, the diabetes management application 14 may communicate the glucose measure in response to a glucose measure request from the remote server 18. The glucose measure request may be a signal communicated over a wireless network from the remote server 18 to the portable computing device on which the diabetes management application 14 resides. The diabetes management application 14 may communicate one glucose measure or multiple glucose measures at a time.

The remote server 18 stores the one or more glucose measures in a memory within the remote server 18. The remote server 18 may perform further processing on the glucose measure. For example, the remote server 18 may associate the glucose measure received with other data relevant to the patient such as patient name, patient age, the date and time the glucose measure was collected, patient measurement history, and any other relevant data. The remote server 18 is configured to allow remote access to the data stored within the remote server 18. For example, the user or a physician of the user may access the glucose measures via a communication network such as the Internet.

Figure 2:
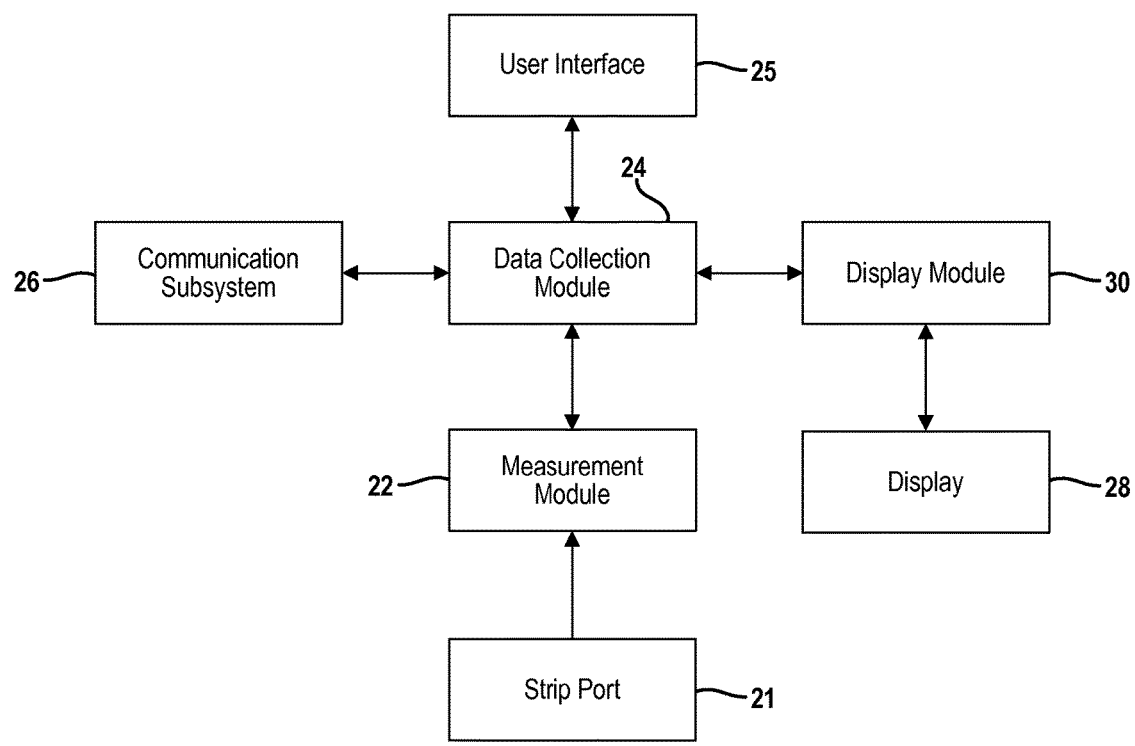
FIG. 2 is a block diagram of an example hardware arrangement for the glucose meter.

With reference to FIG. 2, an example of the glucose meter 12 is presented. The glucose meter 12 may include a measurement module 22, a data collection module 24, and a communication subsystem 26. While the primary components are discussed herein, it is understood that other components (e.g., batteries) may be needed for the overall operation of the glucose meter 12. As used herein, the term module may refer to, be part of, or include an application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above. The term module may further include memory that stores code executed by the processor, where code, as used above, may include software, firmware, and/or microcode, and may refer to programs, routines, functions, classes, and/or objects.

The measurement module 22 cooperatively interacts with a test strip inserted into a strip port 21 to determine a glucose measure from the blood sample on the test strip. The measurement module 22 may include calibration information for the test strips being read by the glucose meter 12.

The data collection module 24 is configured to receive the glucose measure from the measurement module 22 which may in turn be stored in a memory by the data collection module 24. The glucose measure may also be displayed by the data collection module 24 on a display 28. For example, the data collection module 24 may provide the glucose measure to a display module 30. The display module 30 may then control the display 28 to present the glucose measure.

The user can interact with the meter 12 using a user interface 25. The user interface 25 may include components, such as buttons, switches, a speaker, a microphone, USB port, etc. Each of these components is interfaced with the data collection module 24. The data collection module 24 may include a microprocessor and one or more volatile and/or non-volatile memories although other implementations are envisioned for the data collection module 24.

The data collection module 24 is also interfaced with the communication subsystem 26. The communication subsystem 26 may include a wireless transceiver (not shown). The wireless transceiver operates to communicate the glucose measure and other data wirelessly via a communication link to a remote device physically separated from the glucose meter 12, such as the mobile device 16. The communication subsystem 26 can also include an antenna, microcontroller, voltage and power control circuits and a flash memory device.

Figure 3:
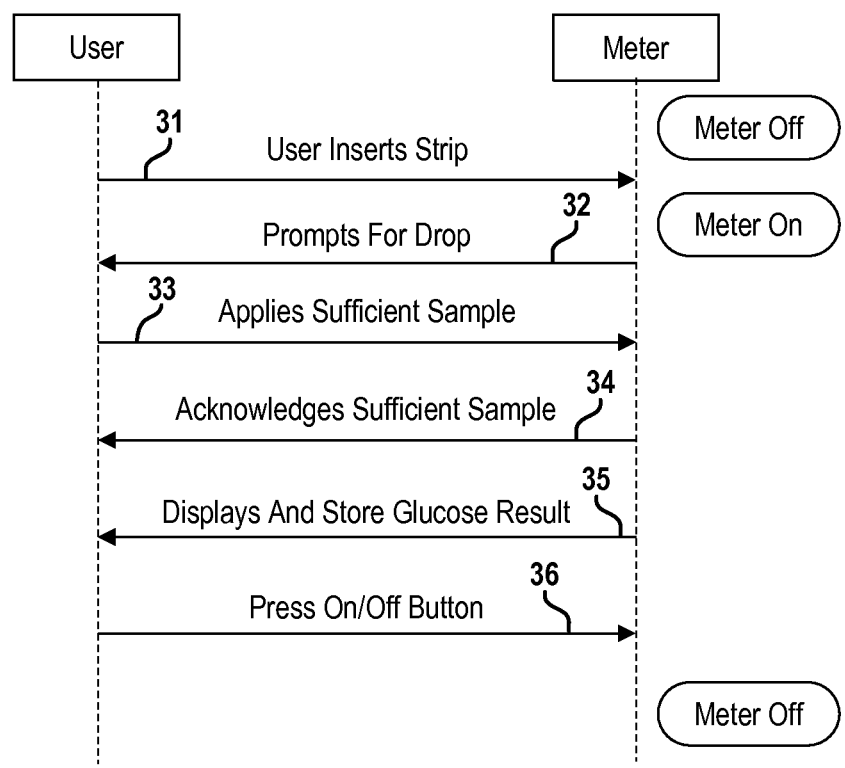
FIG. 3 is a diagram illustrating an example sequence for taking a blood glucose measure using the glucose meter.

With reference to FIG. 3, an example sequence for taking a blood glucose measure using the blood glucose meter 12 is presented. The user may insert a test strip at 31 into a port of the glucose meter 12. Insertion of the test strip prompts the glucose meter 12 to power on. The user may alternatively power on the glucose meter 12 using an on/off button at which point the glucose meter 12 will prompt the user to insert a test strip. The user may also power on the glucose meter 12 without having inserted a test strip into the meter. In any of these cases, the glucose meter 12 may perform a quality check on the test strip inserted into the meter 12. Once the quality check has been completed, the meter 12 is ready to perform a test.

To begin a test, the user is prompted at 32 for a sample of blood. In response to the prompt, the user provides a blood sample at 33 using the test strip, where the test strip includes a reaction site that receives the blood sample from the patient. Upon receipt of the blood sample, the glucose meter 12 proceeds to analyze the blood sample in a manner readily known in the art. Before doing so, the glucose meter 12 may acknowledge the sufficiency of the blood as indicated at 34. During the analysis, a blood glucose measure is obtained from the blood sample.

The blood glucose measure may then be displayed to the user and stored on the glucose meter 12 as indicated at 35. The user may also be prompted to provide additional information regarding the glucose measure. For example, the glucose meter 12 may display a message requesting the user to select an event flag defined by the glucose meter 12. The user may select an appropriate event flag or bypass the message by way of the user interface 25. The user may turn off the glucose meter 12 via the on/off button at 36. Alternatively, the glucose meter 12 may turn off after a preset time period.

Figure 4:
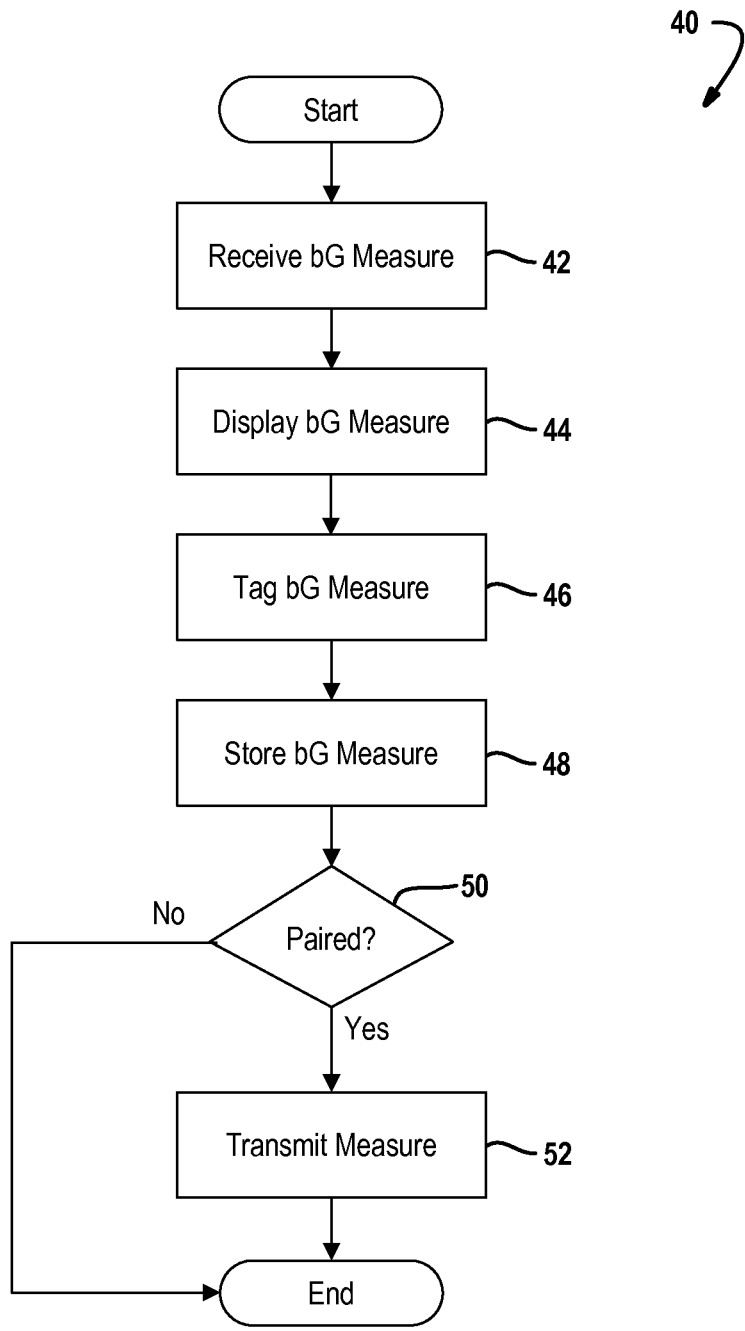
FIG. 4 is a flowchart illustrating an example method for processing and transmitting a blood glucose from the glucose meter.

Upon determining a glucose measure, the measurement module 22 may provide the measurement to the data collection module 24. The data collection module 24 may then tag the glucose measure with identifying information and store the glucose measure. For example, with reference to FIG. 4, a flowchart of an example method 40 for storing glucose measure performed by the data collection module 24 is presented. When the data collection module 24 receives a glucose measure (bG) at 42, the glucose measure is displayed to the user via the display 28 at 44. The data collection module 24 may also prompt the user to provide additional information regarding the glucose meter, if necessary, such as selecting an event flag. The data collection module 24 may then tag the glucose measure with additional information at 46. Once tagged, the glucose measure is stored in the memory of the meter 12 at 48.

The glucose measure may be tagged with a variety of information. For example, the glucose measure may be tagged with a timestamp for when the measure was taken, a serial number of the glucose meter 12 and/or other information pertaining to the test strip. The glucose measure may also include a unique sequence number identifying the glucose measure. For example, a counter may be incremented each time a glucose measure is taken and the value of the counter is assigned to the glucose measure. The sequence number may be used to retrieve missing data from the glucose meter 12 as described further below.

The glucose measure may also be tagged with the event flag inputted by the user via the user interface 25. The event flag associates the glucose measure taken with a particular pre-established activity. For example, the event flag may indicate if the glucose measure was taken before a meal, after a meal, during a fasting period, or before bedtime. The glucose meter 12 may include predefined event flags from which the user may select from via the user interface 25. For example, FIG. 6 provides examples of predefined event flags provided by the glucose meter 12.

Stored glucose measures may be uploaded subsequently from the glucose meter 12 in a batch manner to the portable computing device. Alternatively, the glucose meter 12 may transmit glucose measures individually. For example, at 50 the data collection module 24 may determine whether the glucose meter 12 is paired via wireless communication link with another device, such as the mobile phone 16. If the glucose meter 12 is not paired, the data collection module 24 ends the process until a new glucose measure is received.

If the glucose meter 12 is paired, the data collection module 24 transmits the glucose measure and the tagged information to the device at 52. For example, the glucose measure and the tagged information may be transmitted to the mobile phone 16 or other suitable portable computing devices carried by the user, such as a tablet.

The portable computing device may include a diabetes management application 14 for data analysis as well as other sophisticated diabetes management function. Typically, the portable computing devices such as the mobile phone 16 is in close proximity to the user, and, therefore may be used as a data collector for the user's glucose measures. While the diabetes management application 14 is described as being part of the mobile phone 16, the application 14 and its features as described herein may be utilized on other suitable portable computing devices.

Figure 5:
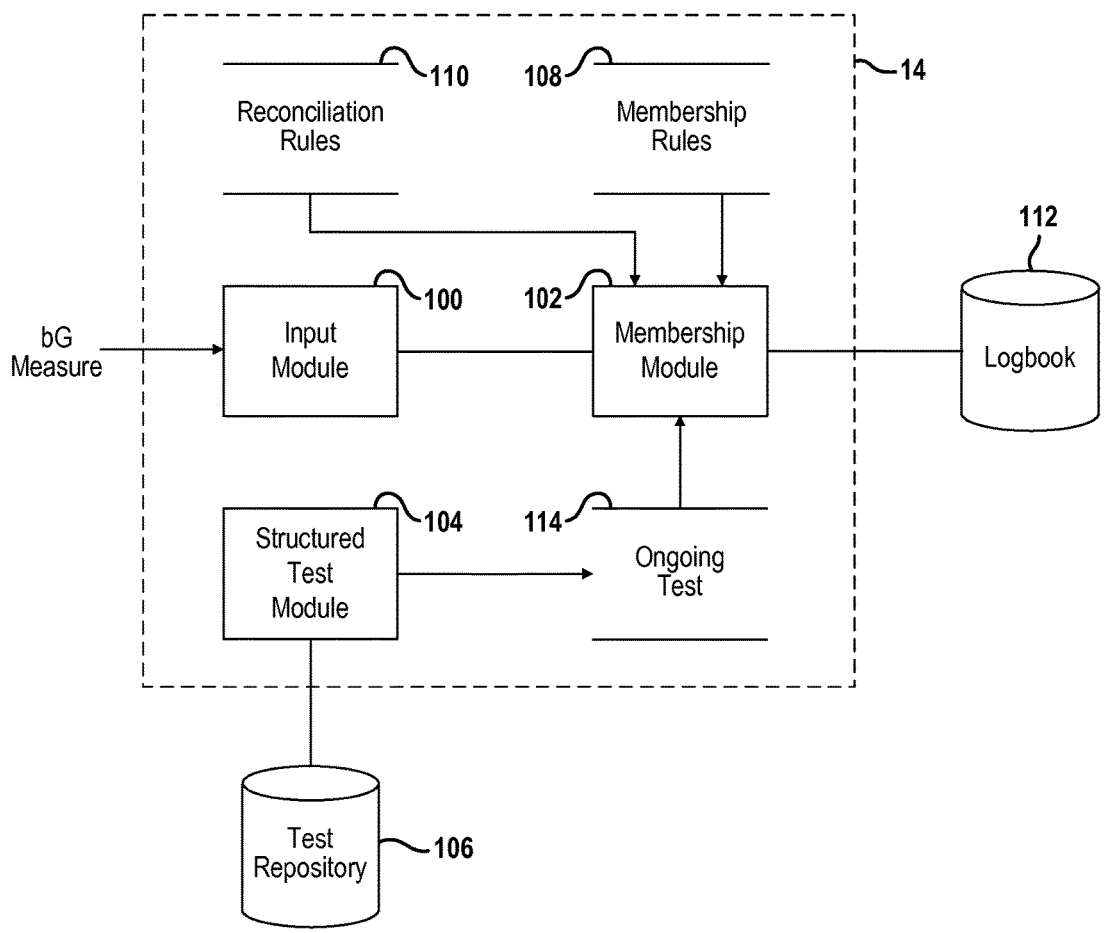
FIG. 5 is a block diagram of an example diabetes management application which resides on the portable computing device.

With reference to FIG. 5, an example of the diabetes management application 14 is presented. Generally, the diabetes management application 14 supports entry, transfer, storage, display and analysis of blood glucose measures and other health indicators. The diabetes management application 14 also provides structured testing procedures to help the user increase their understanding of how to manage their diabetes. Because people tend to carry their portable computing device (e.g., phone) with them, the diabetes management application 14 will provide persons with diabetes an easy-to-use way to capture and track their health information.

The diabetes management application 14 may include an input module 100, a membership module 102, and a structured test module 104. The input module 100 receives data entries from an external device, such as the glucose meter 12. For example, a data entry may be a glucose measure taken by the user. The data entry may include the glucose measure and information tagged with glucose measure. As provided above, the input module 100 of the diabetes management application 14 may receive the data entry directly from the glucose meter 12. Alternatively, the user may input the glucose measure via an interface being displayed on the portable computing device. Using the interface, the user is able to, for example, enter data entries, run structured test, and view a logbook 112 which stores the data entries. The logbook 112 may be residing in a data store on the portable computing device.

While in the example embodiment, the data entry is provided as the glucose measure sent by the glucose meter 12, the data entry may be other information not related to a glucose measure. For example, the data entry may pertain to a meal event, an exercise event or other types of events or health parameters related to the user (also referred to herein as non-blood glucose entries) which can be inputted by the user via the portable computing device.

In the event the data entry includes a glucose measure, the input module may confirm that the diabetes management application 14 has received all the glucose measures up to the glucose measure recently received. For example, the input module 100 may compare the sequence number of the glucose measure recently received with the last glucose measure received. Accordingly, the input module 100 is able to determine if one or more glucose measures are missing, and request the missing glucose measure(s) from the user and/or the glucose meter 12.

After receiving the data entry, the diabetes management system 14 may automatically transmit the data entry to the remote server 18 via a wireless communication link. Transmitting the glucose measure may include packaging the glucose measure in a packet configured to be received and interpreted by the remote server 18. In another embodiment, the diabetes management application 14 may receive a request from the remote server 18 to transmit the data entry to the remote server 18.

The membership module 102 is configured to receive the data entries from the input module 100. The membership module 102 may then associate the data entries with the structured test procedure being managed by the structured test module 104. Specifically, each structured test may be identified with a code. An ongoing test directory 114 may store the code of the structured test being performed by the structured test module 104. Accordingly, the membership module 102 may reference the ongoing test directory 114 to determine which structured test is being performed. The ongoing test directory 114 may reside in a data store on the portable computing device.

The membership module 102 evaluates the data entries with reference to a set of membership rules 108 and reconciliation rules 110, as described below. The membership rules 108 and the reconciliation rules 110 may reside in a data store on the portable computing device. In evaluating the data entries, the membership module 102 determines whether the data entry is to be associated with the structured test being performed. After evaluating the data entry, the data entry may then be inputted by the membership module 102 into a logbook 112 with or without the association.

The structured test module 104 manages a structured test for the user. The structured test specifies one or more collection events for which a glucose measure is required. For simplicity of the explanation set forth below, only one structured test is managed at any given time by the structured test module 104 although it is envisioned that other embodiments could support management of more than one structured test at a time. In any case, the structured tests accessible to the structured test module 104 are stored in a test repository 106 residing on the portable computing device.

In the context of a structured test, glucose measures are typically associated with a user event, such as a meal, exercise, bedtime, etc. Specifically, for a structured test the user measures their blood glucose at specific times relative to certain events which are defined as collection events for the structured test. An acceptance window for the collection event may be defined as a range of times for accepting the blood glucose measure from an expected time for the event. For example, the acceptance window for a pre-meal blood glucose measure may be defined as two hours before the expected meal time (e.g., 7:00 AM to 9:00 AM).

The structured test can specify the acceptance window for a specific collection event as described above. Alternatively, the user may set the acceptance window for the collection event via the interface of the diabetes management application 14. For example, using an input interface of the portable computing device the user may input the acceptance window for breakfast as 8:00 AM to 9:00 AM. It is readily understood that the specified range of acceptance windows may vary depending on the event type. Furthermore, it is understood that the specified ranges may be defined in accordance with medical guidelines and standards.

For illustration purposes, the diabetes management application 14 supports two exemplary structured tests: the testing in pairs (TiP) structured test and the three-day profile structured test. The TiP test involves obtaining a pair of glucose measures in relation to a given event, such as a meal. Specifically, the pair of glucose measures for a given test should fall within a window of time which encapsulates the given event, such that a first measure occurs before the given event (pre-measure) and the second measure occurs after the given event (post-measure). Paired testing can address scenarios such as the relationship between portion sizes and postprandial glucose values, the effect of exercise on blood glucose control and the efficacy of insulin doses.

The three-day profile test involves obtaining glucose measures at predefined timeslots throughout the course of a given day and repeating the measures over a three day period. For example, the three-day profile test specifies obtaining glucose measures at seven different times during the day: pre-breakfast; post-breakfast; pre-lunch; post-lunch; pre-dinner; post-dinner; and bedtime. While reference is made throughout this disclosure to these two particular structured tests, it is readily understood that the concepts disclosed herein are extendable to other types of structured tests.

The central idea behind structured testing is that measuring blood glucose in a structured (as opposed to ad-hoc) way can give the user and health-care provider key insights into improving the user's diabetes management. To complete a structured test, the user must therefore measure their blood glucose at specific times relative to certain events (i.e., a collection event).

When the glucose meter 12 transmit the glucose measure to the mobile phone 16, the diabetes management application 14 assess whether the glucose measure meets a collection event specified by the structured test. While the diabetes management application 14 may remind the user to perform a blood glucose measure, the glucose measure received may not meet the collection event specified by the structured test. In other words, the glucose measure received from the glucose meter 12 may not correspond with the collection events defined.

By way of explanation, the following scenarios are provided as examples of some of the problems encountered when the glucose measure is automatically transmitted. With regard to the TiP test, a glucose measure is needed before and after a particular event as described above. In a first scenario, if the diabetes management application 14 receives a glucose measure having a timestamp of 1:15 PM and no event flag, the glucose measure may be identified as measurement after lunch. However, if a before lunch glucose measure was not received, then the TiP test may not have a complete pair for the lunch event.

In a second scenario, a before lunch glucose measure is received and associated with the TiP test. Subsequently, a second glucose measure is received at 1:15 PM, which may be identified as the after lunch glucose measure. However, the event flag provided with the glucose meal is provided as "before meal". In such a case, the event flag set by the user contradicts the collection event identified for the TiP test. Conversely, in a third scenario, if the second glucose measure is received at 1:15 PM but does not include an event flag, then can it be assumed that the glucose measure received is an after lunch glucose measure?

While the scenarios provided above are related to the TiP test, similar issues can occur with other structured tests. For example, in a fourth scenario where the structured test is the three-day profile test, a glucose measure may be received at 2:00 PM, which matches the timeslot for after lunch. However, the event flag indicates that the glucose measure is a before meal measure. As a result, the event flag provided by the user does not coincide with the timeslot identified by the test. It is readily understood that the rules described herein for addressing the issues related to a glucose measure that does not correspond with the collection event, is not limited to the TiP and three-day profile tests.

The rules used for assessing whether the glucose measure received meets the requirements for a structured test and can be associated with the structured test are outlined in the membership rules 108 and reconciliation rules 110. The membership rules 108 include a set of rules that define the collection events for each structured test. For example, the membership rules 108 may define the user events, such as breakfast, lunch, or dinner, and the expected time of the user event. For example, for the TiP test the membership rules 108 may identify the user events and the acceptance window for the pre- and post-glucose measures for each event.

Similarly, the membership rules 108 define rules for associating a glucose measure for the three-day profile test. For example, per the three-day profile test a glucose measure is required at seven different times per day. The membership rules 108 identify seven timeslots within which a glucose measure is required. Thus, for each of the seven events required under the three-day test, the membership rules 108 define the timeslot (i.e., an acceptance window) for a glucose measure.

In addition to the rules associated with the acceptance window of the collection event, the membership rules 108 may also include other criteria that relate to the specific requirements for the structured test. For example, for the TiP test, the membership rules 108 may assess whether the data entry having the glucose measure forms a completed pair with an existing data entry or whether the data entry will be the only incomplete pair. If the glucose measure forms a complete pair, the glucose measure can be associated with the TiP test. If the glucose measure is an incomplete pair in which the glucose measure is the pre-measure, then the glucose measure may be associated with the TiP test. On the other hand, if the glucose measure is an incomplete pair in which the glucose measure is the post-measure, then the glucose measure may just be stored in the logbook 112 and may not be associated with the TiP test.

By way of further explanation, the membership rules 108 may include similar rules for the three-day profile test. For example, the membership rules 108 may assess whether the data entry having the glucose measure is identified for the collection event identified by the three-day profile test. If the glucose measure is for a different collection event, the glucose measure is not associated with the three-day profile test. On the other hand if the glucose measure is for the same collection event then the glucose measure is associated with the three-day profile test.

The reconciliation rules 110 define a set of rules that resolve potential conflicts between the glucose measure and the structured test based on the event flag received with the glucose measure. Specifically, the event flag predefined by the glucose meter 12 may not clearly identify which collection event the glucose measure relates to. For example, with reference to FIG. 6, the event flag defined by the glucose meter 12 may simply identify a glucose measure as before meal, after meal, fasting, bedtime, or other. Whereas, flags for a structured test specify collection events as, for example, before breakfast, before lunch, before teatime, before dinner, etc.

The reconciliation rules 110 reconcile the event flags of the glucose meter 12 with the flags of a structured test by way of a predefined correlation. For example, the reconciliation rules 110 may include an event flag reconciliation table similar to the one shown in FIG. 6. The event flag reconciliation table correlates the event flags of the glucose meter 12 with structured test flags. Specifically, the event flag reconciliation table identifies structured test flags that are compatible and incompatible with a given event flag from the glucose meter 12.

By way of explanation, if the event flag is provided as "After Meal", the event flag is compatible with structured test flags: "After Breakfast", "After Lunch", "After Teatime", "After Dinner", "Low bG", "High bG", "After Low bG", "After High bG". Conversely, the event flag "After Meal" is incompatible with: "Before Breakfast", "Before Lunch", "Before Teatime", "Before Dinner", and "Bedtime". Accordingly, a general event flag provided by the glucose meter 12 may be matched to a specific collection event of a structured test. While the reconciliation rules 110 may correlate the event flags defined by the glucose meter 12 with the structured test flags in the form of a table, it is readily understood that other methods may be used to correlate the event flags and the structured test.

The reconciliation rules 110 may include other rules that correlate the event flags of the glucose meter 12 with specific collection event. For example, the event flag set by the glucose meter 12 may be changed to a compatible structured test flag. On the other hand, an event flag cannot be change to an incompatible structured test flag. The reconciliation rules 110 are designed to defer to the user's selection. In other words, the reconciliation rules select the event flag set by the user when there is a conflict between the event flag and the structured test flag for the collection event. Furthermore, in a case where the glucose measure does not include an event flag, the reconciliation rules 110 may define a default flag for the glucose measure based on, for example, the timestamp of the glucose measure and/or the collection event of the structured test. For instance, if the glucose measure was received at 8:00 PM and the collection event is for post-dinner measure, then the glucose measure may be flagged as "After Dinner".

The membership module 102 utilizes the membership rules 108 and the reconciliation rules 110 when associating the data entry received with a structured test. By way of explanation, example methods for processing and associating a data entry received by the diabetes management application 14 from an external device, such as the glucose meter 12, is presented below.

Figure 7:
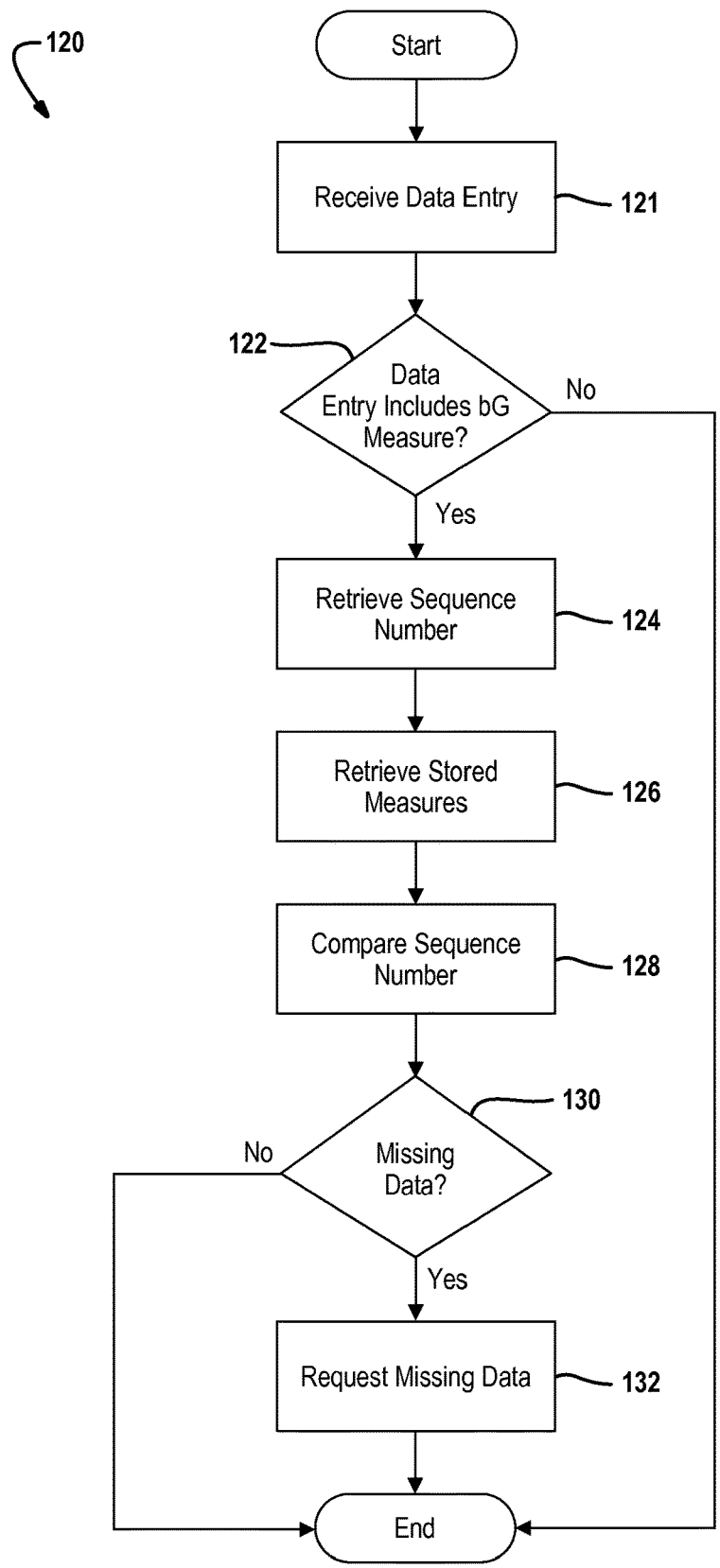
FIG. 7 is a flowchart illustrating an example method performed by the diabetes management application for processing a data entry.

With reference to FIG. 7, an example method 120 for processing a data entry which can be performed by the input module 100 is presented. Upon receiving a data entry at 121, the input module 100 determines whether the data entry includes a glucose measure (bG) at 122. If the data entry does not include a glucose measure, the method ends and the data entry is provided to the membership module 102. If a glucose measure is included, the sequence number associated with the glucose measure is retrieved at 124. As described above, a unique sequence number is assigned to each glucose measure by the glucose meter 12. Thus, the sequence number associated with the glucose measure can be extracted from the data packet or message received from the glucose meter 12.

The input module 100 retrieves one or more stored glucose measure from a memory at 124. For example, a series of glucose measures previously received from the glucose meter 12, along with their associated sequence numbers, may be stored in the memory of the portable computing device. Alternatively, only the most recently received glucose measure and its sequence number may be stored in the portable computing device. In either case, the glucose measure(s) stored in the portable computing device along with associated sequence number(s) are retrieved at 126.

The input module 100 then compares the sequence number extracted from the glucose measure received and the sequence number of the stored glucose measure(s) at 128. The input module 100 may determine whether data regarding a glucose measure is missing at 130. If data is missing, the input module 100 transmits a request for missing glucose measures to the glucose meter 12 at 132. For example, a request for missing glucose measures is transmitted when the extracted sequence number is 74 and the highest stored sequence number is 71. Conversely, a request is not transmitted when the extracted sequence number is 74 and the highest stored sequence number is 73. In other embodiments, the diabetes management application 14 via the input module 100 may analyze the series of glucose measures for omitted measures and send a request for each glucose measure missing from the series of glucose measures. In response to the request, the glucose meter 12 may transmit the missing glucose measure to the diabetes management system 14.

Figure 8:
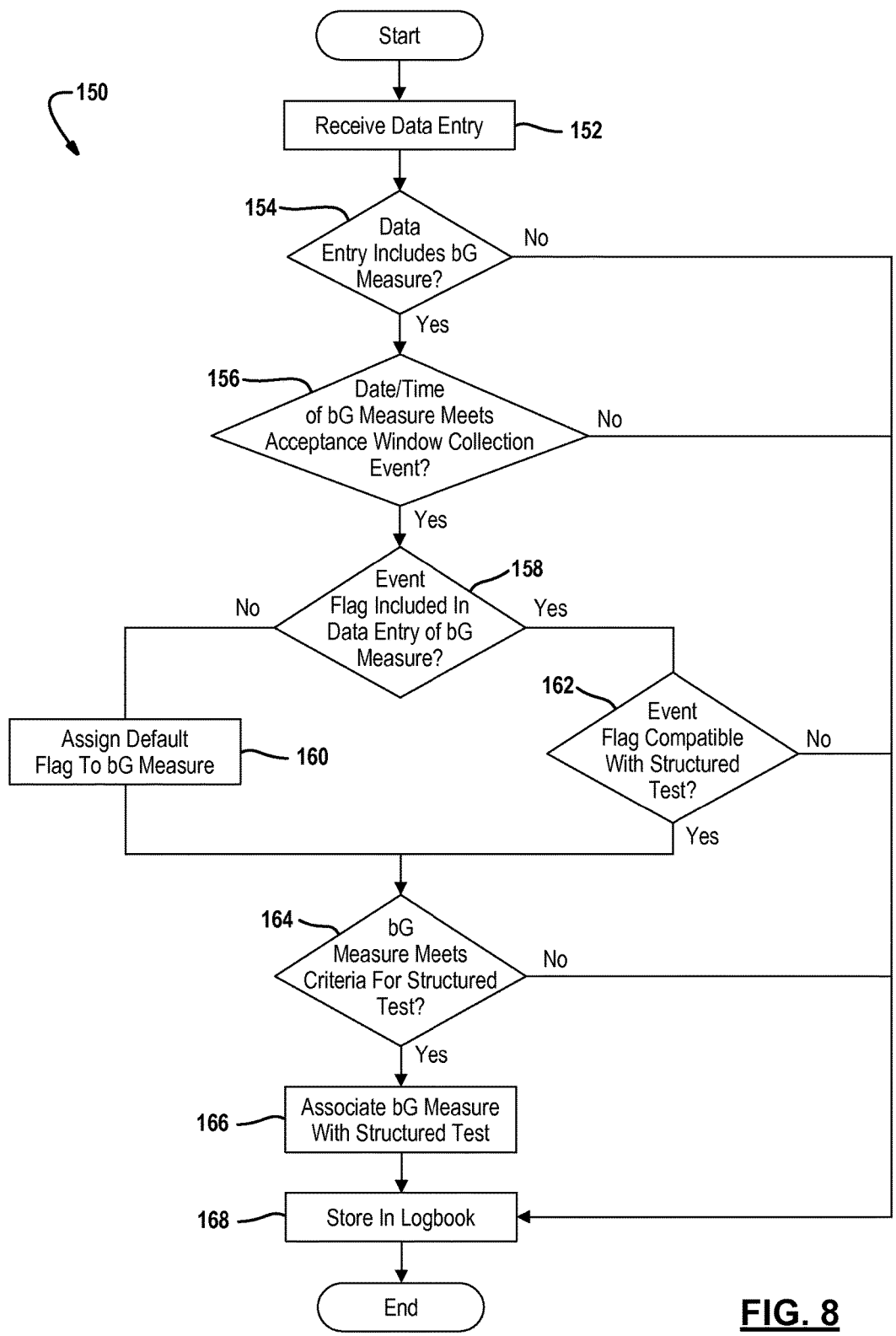
FIG. 8 is a flowchart illustrating an example method performed by the diabetes management application for reconciling a glucose measure received from the glucose meter with a structured test.

With reference to FIG. 8 an example method for evaluating a glucose measure which may be implemented by the membership module 102 is presented. Upon receiving a data entry at 152, the membership module 102 determines whether the data entry includes a glucose measure at 154. If the glucose measure is not included, the membership module 102 stores the data entry in the logbook 112 at 168. In the example embodiment, both the input module 100 and the membership module 102 determine if the data entry includes the glucose measure. Alternatively, once the input module 100 determines that the data entry does not include the glucose measure, the input module 100 may store the data entry in the logbook 112, and only provide the data entry with the glucose measure to the membership module 102. Thus, the method 150 may start at 156.

When the data entry includes the glucose measure, the membership module 102 determines whether the time at which the glucose measure was taken matches an acceptance window for a collection event of the structured test being performed at 156. For example, the membership module 102 may refer to the membership rules 108 and retrieve the rules associated with the structured test being performed. The membership module 102 compares the timestamp of the glucose measure with the acceptance windows defined for various collection events of the structured test. If the glucose measure falls within the acceptance window of a collection event, the membership module 102 continues to 158. On the other hand, if the glucose measure does not fall within the acceptance window of a collection event, the data entry is stored in the logbook 112 at 168.

The membership module 102 determines whether an event flag is included in the data entry of the glucose measure at 158. If the event flag is not included, the membership module 102 assigns the glucose measure a default flag based on the reconciliation rules 120 at 160. More particularly, based on the identified collection event and/or the date/time of the glucose measure, the membership module 102 may set the default flag as one of the structured test flag. For example, the glucose measure was taken within the acceptance window of a particular collection event, such as for pre-breakfast, then the membership module 102 may set the flag as "Before Breakfast". After setting the default flag, the membership module 102 continues to 164.

When the event flag is included in the data entry, the membership module 102 determines whether the event flag is compatible with the structured test by referencing the reconciliation rules 110 at 162. Specifically, the membership module 102 determines whether the event flag of the glucose measure is compatible with the structured test flag for the collection event. For example, if the event flag is "Before Meal" and the collection event is for a glucose measure before breakfast, the event flag is compatible with the structured test flag "Before Breakfast". On the other hand, if the event flag is "Before Meal" and the collection event is for a glucose measure after lunch, then the event flag is incompatible with the structured test flag "After Lunch". Specifically, the event flag cannot be changed to or correlated with an incompatible flag.

If the event flag is not compatible with the structured test, the membership module 102 stores the data entry in the logbook 112 at 168. On the other hand if the event flag is compatible with the structured test, the membership module 102 continues to 164.

At 164 the membership module 102 determines whether the glucose measure received meets the criteria for the structured test being performed as defined by the membership rules 108. For example, if the structured test is the TiP test, the membership module 102 may determine whether the glucose measure received forms a completed pair with an existing glucose measure or whether the glucose measure is the first measure of the pair (i.e., only incomplete pair). If the glucose measure forms the completed pair or is the pre-measure for the pair, then the glucose measure is associated with the TiP test. If the glucose measure is the post-measure but no pre-measure is provided then the glucose measure received is not associated with the TiP test and the glucose measure is stored in the logbook 112.

By way of another example, if the structured test is the three day profile test, the membership module 102 may determine whether the event flag of the glucose measure indicates the collection event of an identified timeslot. For example, if the event flag for the glucose measure is pre-meal, and the collection event is pre-lunch measurement, then the membership module 102 may associate the glucose measure with the three-day profile test. Alternatively, if the event flag is post-meal and the collection event is pre-meal then the membership module 102 may not associate the glucose measure with three-day profile test.

If the glucose measure does not meet the association criteria of the structured test, the membership module 102 stores the data entry in the logbook 112 at 168. If the glucose measure does meet the association criteria then the membership module 102 associates the glucose measure with the structured test at 166 and stores the data entry in the logbook 112 at 168. For example, the membership module 102 may include the code associated with the structured test being performed with the data entry of the glucose measure received. The data entry is then stored in the logbook 112 at 168.

Using the membership rules 108 and the reconciliation rules 110, an operation of the membership module 102 with regard to the scenarios described above are now explained. As to the first scenario, the membership module receives a glucose measure having a timestamp of 1:15 PM and no event flag. The structured test being performed is identified as the TiP test, and the acceptance window within which the glucose measure falls within is identified as an after lunch measure. Since, the glucose measure does not include an event flag, the membership module 102 assigns the glucose measure a default flag of "After Lunch". Based on the membership rules 108, the membership module 102 determines that the glucose measure for the pre-lunch measure was not received, and therefore, the glucose measure for the post-lunch measure would be part of an incomplete pair. Accordingly, the membership module 102 does not associate the glucose measure received with the TiP test.

As to the second scenario, the same glucose measure is received as described in the first scenario, except that the glucose measure includes an event flag provided as "before meal". The acceptance window within which the glucose measure falls within is identified as an after lunch measure. Since, the event flag is "before meal", the event flag is incompatible with the structured test flag, which is "After Lunch". Therefore, the glucose measure is not associated with the TiP test even though a pre-lunch measure is stored.

For the third scenario, the same glucose measure is received as described in the first scenario. Since the glucose measure does not include an event flag, a default flag is set as "After Lunch". Based on the membership rules 108, the membership module 102 determines that the glucose measure for the pre-lunch measure was received, and therefore, the glucose measure for the post-lunch measure would complete the pair. Accordingly, the glucose measure which was assigned the default flag is associated with the TiP test.

In the fourth scenario, the structured test being performed is the three-day profile test. The membership module 102 receives a glucose measure having a timestamp of 2:00 PM, which matches an acceptance window for the timeslot for after lunch. However, the event flag indicates that the glucose measure is a before meal measure. As a result, the event flag is incompatible with the structured test event flag, and therefore, the glucose measure is not associated with the three-day profile test.

In addition to or in lieu of automatically storing a glucose measure having an incompatible event flag, the membership module 102 may prompt the user to confirm the event flag set by the user. For example, if the event flag is originally set as "before meal" but is provided within an acceptance window of for a after breakfast, the user may be asked to confirm that the glucose measure is for before meal. Thus, allowing the user to correct any misidentified glucose measure.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific devices and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, steps, operations, and/or components, but do not preclude the presence or addition of one or more other features, steps, operations components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. A method for analyzing diabetes related information by a diabetes management application residing on a computing device, the method comprising:

retrieving, by the diabetes management application residing on the computing device wherein the diabetes management application is implemented as computer executable instructions executed by a computer processor of the computing device, a subject structured test selected from a plurality of structured tests, wherein the plurality of structured tests are stored in a test repository on the computing device, and wherein each of the plurality of structured tests specifies one or more collection events at which a glucose measurement is required for a given structured test;

receiving, by the diabetes management application residing on the computing device, a data entry from a blood glucose meter via a communication link between the computing device and the blood glucose meter, wherein the data entry includes a glucose measurement, a timestamp indicating a time at which the glucose measurement was taken, and an indicator of a pre-established activity associated with the glucose measurement;

evaluating, by the diabetes management application residing on the computing device, the data entry in relation to the subject structured test in part by comparing the indicator of the pre-established activity of the data entry with the one or more collection events specified by the subject structured test;

determining, by the diabetes management application residing on the computing device, a presence or an absence of a value in the indicator of the pre-established activity of the data entry, and wherein the absence of the value in the indicator of the pre-established activity of the data entry is determined, assigning, by the diabetes management application residing on the computing device, a default value to the indicator of the pre-established activity of the data entry;

identifying, by the diabetes management application residing on the computing device, the data entry as compatible with the subject structured test when the value in the indicator of the pre-established activity of the data entry correlates with a value of a given collection event specified by the subject structured test;

identifying, by the diabetes management application residing on the computing device, the data entry as non-compatible with the subject structured test when the value in the indicator of the pre-established activity of the data entry does not correlate with the value of the given collection event specified by the subject structured test;

inputting, by the diabetes management application residing on the computing device, the data entry with an association to the subject structured test into a logbook residing in a data store on the computing device when the data entry is compatible with the subject structured test; and inputting, by the diabetes management application residing on the computing device, the data entry without the association to the subject structured test into the logbook residing in the data store on the computing device when the data entry is not compatible with the subject structured test.

2. The method of claim 1, wherein the indicator of the pre-established activity is an event flag that identifies the pre-established activity, and wherein the event flag is one of multiple predefined event flags defined by the blood glucose meter.

3. The method of claim 1, wherein evaluating the data entry in relation to the subject structured test further comprises:

determining, by the diabetes management application residing on the computing device, whether the indicator of the pre-established activity includes an event flag, wherein the event flag indicates the pre-established activity, and wherein the event flag is one of multiple predefined event flags defined by the blood glucose meter; and evaluating, when the indicator of the pre-established activity includes the event flag, by the diabetes management application residing on the computing device, the event flag by comparing the event flag with multiple structured test flags for the subject structured test, wherein a subject structured test flag is one of the multiple structured test flags, and wherein:

the data entry correlates with the given collection event specified by the subject structured test when the event flag is compatible with the subject structured test flag defined for the given collection event specified by the subject structured test, and the data entry does not correlate with the given collection event specified by the subject structured test when the event flag is incompatible with the subject structured test flag defined for the given collection event specified by the subject structured test.

4. The method of claim 3, wherein evaluating the data entry in relation to the subject structured test further comprises:

associating, when the indicator of the pre-established activity does not include the event flag, by the diabetes management application residing on the computing device, a default flag with the glucose measurement based on the timestamp indicating the time at which the glucose measurement was taken, wherein the default flag is one of the multiple structured test flags.

5. The method of claim 1, further comprising:

evaluating, by the diabetes management application residing on the computing device, the data entry in relation to the subject structured test using a membership rule set, wherein the membership rule set defines rules for associating the data entry with the subject structured test; and associating, by the diabetes management application residing on the computing device, the data entry with the subject structured test when the data entry is identified as compatible with the subject structured test, and when the data entry satisfies a rule of the membership rule set.

6. The method of claim 5, wherein the membership rule set further comprises:

a first rule that does not associate a data entry with the subject structured test when a glucose measurement of the data entry is outside of an acceptance window for a collection event specified by the subject structured test, wherein the acceptance window defines a period of time within which a glucose measurement is required for the collection event specified by the subject structured test; and a second rule that associates the data entry with the subject structured test when the glucose measurement of the data entry is within the acceptance window for the collection event specified by the subject structured test, wherein the data entry correlates with the collection event specified by the subject structured test.

7. The method of claim 1, wherein the indicator of the pre-established activity includes the timestamp indicating the time at which the glucose measurement was taken, and wherein the method further comprises:

comparing, by the diabetes management application residing on the computing device, the timestamp indicating the time at which the glucose measurement was taken with an acceptance window for the given collection event specified by the subject structured test, wherein the acceptance window defines a period of time within which the glucose measurement is required for the given collection event specified by the subject structured test; and inputting, by the diabetes management application residing on the computing device, the data entry into the logbook without identifying whether the data entry is compatible or non-compatible with the subject structured test when the timestamp of the glucose measurement is outside the acceptance window for the given collection event specified by the subject structured test.

8. The method of claim 1, wherein the indicator of the pre-established activity includes the timestamp and an event flag, wherein the timestamp indicates the time at which the glucose measurement was taken, wherein the event flag indicates the pre-established activity, and wherein the event flag is one of multiple predefined event flags defined by the blood glucose meter.

9. The method of claim 1, further comprising:

determining, by the diabetes management application residing on the computing device, whether the indicator of the pre-established activity includes an event flag that indicates the pre-established activity, wherein the event flag is one of multiple predefined event flags defined by the blood glucose meter;

determining, when the indicator of the pre-established activity includes the event flag, by the diabetes management application residing on the computing device, whether the data entry correlates with the collection event specified by the subject structured test based on the event flag and a reconciliation rule set, wherein the reconciliation rule set defines rules for resolving conflicts between the glucose measurement and the subject structured test based on the event flag received with the glucose measurement; and setting, by the diabetes management application residing on the computing device, a default flag based on the timestamp indicating the time at which the glucose measurement was taken when the indicator of the pre-established activity does not include the event flag, wherein the default flag is one of multiple structured test flags defined for the subject structured test.

10. The method of claim 9, wherein the reconciliation rule set further comprises:

a first rule that correlates a data entry with a collection event specified by the subject structured test when an indicator of a pre-established activity is compatible with a subject structured test flag for a collection event specified by the subject structured test, wherein the structured test flag is one of multiple structured test flags defined for the subject structured test; and a second rule that does not correlate the data entry with the collection event specified by the subject structured test when the indicator of the pre-established activity is incompatible with the subject structured test flag for the collection event specified by the subject structured test.

11. A system for analyzing diabetes related information by a diabetes management application residing on a computing device, comprising:

the computing device comprising a memory and a processor;

the diabetes management application residing on the computing device, wherein the diabetes management application is comprised of a plurality of modules and implemented as computer executable instructions stored in the memory; and the processor configured to execute the instructions stored in the memory to perform the steps of:

administer, by a structured test module, a subject structured test selected from a plurality of structured tests, wherein the plurality of structured tests are stored in a test repository on the computing device, and wherein each of the plurality of structured tests specifies one or more collection events at which a glucose measurement is required for a given structured test;

receive, by an input module, a data entry from a blood glucose meter via a communication link between the computing device and the blood glucose meter, wherein the data entry includes a glucose measurement, a timestamp indicating a time at which the glucose measurement was taken, and an indicator of a pre-established activity associated with the glucose measurement;

receive, by a membership module, the data entry from the input module;

evaluate, by the membership module, the data entry in relation to the subject structured test in part by comparing the indicator of the pre-established activity of the data entry with the one or more collection events specified by the subject structured test;

determine, by the membership module, a presence or an absence of a value in the indicator of the pre-established activity of the data entry, and wherein the absence of the value in the indicator of the pre-established activity of the data entry is determined, assigning, by the membership module, a default value to the indicator of the pre-established activity of the data entry;

identify, by the membership module, the data entry as compatible with the subject structured test when the value in the indicator of the pre-established activity of the data entry correlates with a value of a given collection event specified by the subject structured test;

identify, by the membership module, the data entry as non-compatible with the subject structured test when the value in the indicator of the pre-established activity of the data entry does not correlate with the value of the given collection event specified by the subject structured test;

input, by the membership module, the data entry with the association to the subject structured test into a logbook residing in a data store on the computing device when the data entry is compatible with the subject structured test; and input, by the membership module, the data entry without the association to the subject structured test into the logbook residing in the data store on the computing device when the data entry is not compatible with the subject structured test.

12. The system of claim 11, wherein the indicator of the pre-established activity is an event flag that identifies the pre-established activity, and wherein the event flag is one of multiple predefined event flags defined by the blood glucose meter.

13. The system of claim 11, wherein evaluating the data entry in relation to the subject structured test further comprises:

determine, by the membership module, whether the indicator of the pre-established activity includes an event flag, wherein the event flag indicates the pre-established activity, and wherein the event flag is one of multiple predefined event flags defined by the blood glucose meter; and evaluate, when the indicator of the pre-established activity includes the event flag, by the membership module, the event flag by comparing the event flag with multiple structured test flags for the subject structured test, wherein a subject structured test flag is one of the multiple structured test flags, and wherein:

the data entry correlates with the given collection event specified by the subject structured test when the event flag is compatible with the subject structured test flag defined for the given collection event specified by the subject structured test, and the data entry does not correlate with the given collection event specified by the subject structured test when the event flag is incompatible with the subject structured test flag defined for the given collection event specified by the subject structured test.

14. The system of claim 13, wherein evaluating the data entry in relation to the subject structured test further comprises:

associate, when the indicator of the pre-established activity does not include the event flag, by the membership module, a default flag with the glucose measurement based on the timestamp indicating the time at which the glucose measurement was taken, wherein the default flag is one of the multiple structured test flags.

15. The system of claim 11, further comprising:

evaluate, by the membership module, the data entry in relation to the subject structured test using a membership rule set, wherein the membership rule set defines rules for associating the data entry with the subject structured test; and associate, by the membership module, the data entry with the subject structured test when the data entry is identified as compatible with the subject structured test, and when the data entry satisfies a rule of the membership rule set.

16. The system of claim 15, wherein the membership rule set further comprises:

a first rule that does not associate a data entry with the subject structured test when a glucose measurement of the data entry is outside of an acceptance window for a collection event specified by the subject structured test, wherein the acceptance window defines a period of time within which a glucose measurement is required for the collection event specified by the subject structured test; and a second rule that associates the data entry with the subject structured test when the glucose measurement of the data entry is within the acceptance window for the collection event specified by the subject structured test, wherein the data entry correlates with the collection event specified by the subject structured test.

17. The system of claim 11, wherein the indicator of the pre-established activity includes the timestamp indicating the time at which the glucose measurement was taken, and wherein the system further comprises:

compare, by the membership module, the timestamp indicating the time at which the glucose measurement was taken with an acceptance window for the given collection event specified by the subject structured test, wherein the acceptance window defines a period of time within which the glucose measurement is required for the given collection event specified by the subject structured test; and input, by the membership module, the data entry into the logbook without identifying whether the data entry is compatible or non-compatible with the subject structured test when the timestamp of the glucose measurement is outside the acceptance window for the given collection event specified by the subject structured test.

18. The system of claim 11, wherein the indicator of the pre-established activity includes the timestamp and an event flag, wherein the timestamp indicates the time at which the glucose measurement was taken, wherein the event flag indicates the pre-established activity, and wherein the event flag is one of multiple predefined event flags defined by the blood glucose meter.

19. The system of claim 11, further comprising:

determine, by the membership module, whether the indicator of the pre-established activity includes an event flag that indicates the pre-established activity, wherein the event flag is one of multiple predefined event flags defined by the blood glucose meter;

determine, when the indicator of the pre-established activity includes the event flag, by the membership module, whether the data entry correlates with the collection event specified by the subject structured test based on the event flag and a reconciliation rule set, wherein the reconciliation rule set defines rules for resolving conflicts between the glucose measurement and the subject structured test based on the event flag received with the glucose measurement; and set, by the membership module, a default flag based on the timestamp indicating the time at which the glucose measurement was taken when the indicator of the pre-established activity does not include the event flag, wherein the default flag is one of multiple structured test flags defined for the subject structured test.

20. The system of claim 19, wherein the reconciliation rule set further comprises:

a first rule that correlates a data entry with a collection event specified by the subject structured test when an indicator of a pre-established activity is compatible with a subject structured test flag for a collection event specified by the subject structured test, wherein the structured test flag is one of multiple structured test flags defined for the subject structured test; and a second rule that does not correlate the data entry with the collection event specified by the subject structured test when the indicator of the pre-established activity is incompatible with the subject structured test flag for the collection event specified by the subject structured test.

* * * * *